United States Patent [19]

Van Veen

[11] Plant 4,992

[45] Mar. 15, 1983

[54] ROSE PLANT

[75] Inventor: Jan Van Veen, Aalsmeer, Netherlands

[73] Assignee: Carlton Rose Nurseries, Inc., Carlton, Oreg.

[21] Appl. No.: 297,743

[22] Filed: Aug. 31, 1981

[51] Int. Cl.[3] ..... A01H 5/00

[52] U.S. Cl. ..... Plt./21

[58] Field of Search ..... Plt./20, 21

*Primary Examiner*—James R. Feyrer

*Attorney, Agent, or Firm*—Chernoff & Vilhauer

[57] ABSTRACT

A rose plant of the Hybrid Tea Class obtained as a seedling from a seed parent of the Ilone variety and an unnamed pollen parent provides long lasting blooms which maintain their true color from bud through leaf petal, on a continuous basis in a greenhouse.

17 Drawing Figures

BACKGROUND AND SUMMARY OF THE INVENTION

The present invention relates to a new and distinct variety of Hybrid Tea rose plant, a seedling resulting from a definite effort to produce an improvement in this class of rose.

The primary feature of this new variety which connotates its distinctive advance over existing types are its ability to freely yield a quantity of cut flower under greenhouse conditions which maintain true color after being cut, from bud through petal drop.

The variety of rose plant of the present invention was obtained at Aalsmeer, Holland, as a seedling from a seed parent of the Ilona variety (not patented in the United States) and an unnamed pollen parent (seedling 884 × seedling 1693). The crossing was made during 1976, the sowing during 1977, and the first flower appeared during 1977.

Asexual reproduction of my new and distinct variety shows that its unique combination of characteristics come true to form and are established and transmitted through succeeding propagations by grafting and by budding.

BRIEF DESCRIPTION OF THE DRAWINGS

The accompanying photographs shown typical specimens of the vegetative growth and flowers of the new variety in different stages of development and are depicted in color as nearly true as is reasonably possible the make the same in color illustrations of this character:

FIG. 1 is a developing bud;

FIG. 2 shows a flower when starting to open;

FIG. 3 shows a nearly open flower;

FIG. 4 shows a stem with branches;

FIG. 5 shows a cross-section of a fully open flower with the stamens, pistils, and receptacle showing;

FIG. 6 shows an outer petal (inside surface);

FIG. 7 shows an outer petal (outside surface);

FIG. 8 shows an intermediate petal (inside surface);

FIG. 9 shows an intermedite petal (outside surface);

FIG. 10 shows an inner petal (inside surface);

FIG. 11 shows an inner petal (outside surface);

FIG. 12 shows a receptacle with the stamens removed and pistils showing;

FIG. 13 shows one of the leaves with a composition of three leaflets showing the upper surface;

FIG. 14 shows one of the leaves with a composition of five leaflets showing the upper surface;

FIG. 15 shows one of the leaves with a composition of five leaflets showing the under surface;

FIG. 16 shows a fruit with seeds;

FIG. 17 shows a composite of several flowers in different stages of development.

DETAILED DESCRIPTION OF THE DISCLOSURE

The following description was made during September, 1979 of the rose plants of the new and distinct variety growing in a greenhouse at Aalsmeer, Holland. Color designations are to *The Wilson Color Chart I and II.*

FLOWER

Flowers borne: Two to three in a flat cluster on long, strong stems.

Quantity of bloom: Abundant in greenhouse.

Continuity: Continuous.

Fragrance: Slight; tea.

Bud:

*Peduncle.*—Medium length; medium weight; erect; medium green; entirely smooth.

*Before calyx breaks.*—Size: medium. Form: ovoid with a conspicuous neck; with foliaceous appendages on the surface of the bud; with slender foliaceous parts extending beyond the tip of the bud equal to ½ of its length.

*As calyx breaks.*—Color: Cardinal Red HCC 822.

*As first petal opens.*—Color: Outside: Cardinal Red HCC 822. Inside: Velvet Cardinet Red HCC 822. Opening: It does open up well.

Bloom:

*Size when fully open.*—Large; 4 inches to 4½ inches.

*Petalage.*—Double; from 30 to 35 petals; arranged regularly.

*Form.*—Very high centered globular at first; becoming open high centered; petals remaining at first loosely rolled outward; becoming later at maturity flat rolled outward.

Petals: Medium thick; with inside velvety; outside satiny.

*Shape.*—Outer: Ovate — undulate; base flat; with one notch. Intermediate: Ovate — undulate; apex flat; with one tooth. Inner: Ovate — undulate; apex flat; with one notch.

*Color.*—Colors may be modified by being shaded with other colors. Color of newly opened flower: Outer petal: Outside surface: Cardinal Red HCC 822. Inside surface: Cardinal Red HCC 822; very velvety. Intermediate petal: Outside surface: Cardinal Red HCC 822. Inside surface: Cardinal Red HCC 822; very velvety. Inner petal: Outside surface: Cardinal Red HCC 822. Inside surface: Cardinal Red HCC 822; very velvety. Color of flowers three days after opening: Outer petal: Outside surface: Current Red HCC 821/1. Inner petal: Outside surface: Current Red HCC 821. Inside surface: Current Red HCC 821/1; velvety. General color effect: Newly opened flower: Cardinal Red HCC 822; velvety. Flowers three days open: Current Red HCC 821. Behavior: Drop off cleanly. Flower longevity: Cut roses grown in greenhouse kept at living room temperature 6 days during September.

REPRODUCTIVE ORGANS

Stamens: Medium number; arranged irregularly about pistils.

Filaments: Many; with anthers; medium length.

*Color.*—Carmin HCC 21/1.

Anthers: Open at various times; medium size.

*Color.*—Egyptian Buff HCC 407. Seldom fused with a petaloid.

Pollen: Abundant; yellow-gold.

Pistils: Many.

Styles: Uneven; medium length; medium thickness; bunched.

Stigma: Yellow.

Ovaries: Some protruding from receptacle.

Hips: Medium; very smooth; thick fleshy walls; green.

Sepals: Permanent; medium long; spear-shaped; recurved.

Seeds: Few; large.

PLANT

Foliage:

*Leaves.*—Compound of 3 and 5 leaflets; normal quantity; medium size; leathery.

*Leaflet.*—Shape: ovoid; apex acuminative; base margin simply serrate. Color: Mature upper surface: Spinach Green HCC 0960/1. Mature under surface: Willow Green HCC 000862/1. Young upper surface: Parsley Green HCC 00962/2. Young under surface: Willow Green HCC 000862/3.

*Rachis.*—Medium. Upper side: smooth grooved. Under side: moderately thorny.

*Stipules.*—Medium length; narrow width; with medium long points; turning out at an angle of more than 45°; recurved toward the stem.

*Disease.*—Resistance comparable to the average variety growing under the same cultural conditions.

GROWTH

Habit: Upright; branched.

Growth: Moderately vigorous.

Canes: Moderately heavy.

Main stems:

*Color.*—Fern Green HCC 0862.

*Prickles.*—Several. Color: Erythrite Red HCC 0027. Hairs: none.

Branches: Dull.

*Color.*—Fern Green HCC 0862/1.

*Prickles.*—Few.

*Hairs.*—None.

New shoots:

*Color.*—Scheeles Green HCC 860/1.

*Prickles.*—Few. Color: Erythrite Red HCC 0027/1.

*Hairs.*—None.

I claim:

1. A new and distinct variety of rose plant of the Hybrid Tea Class obtained as a seedling from a seed parent of the Ilona class and an unnamed pollen parent characterized by its ability to yield large long lasting blooms on a continuous basis in a greenhouse which maintain true color from bud through petal drop, substantially as shown as described.

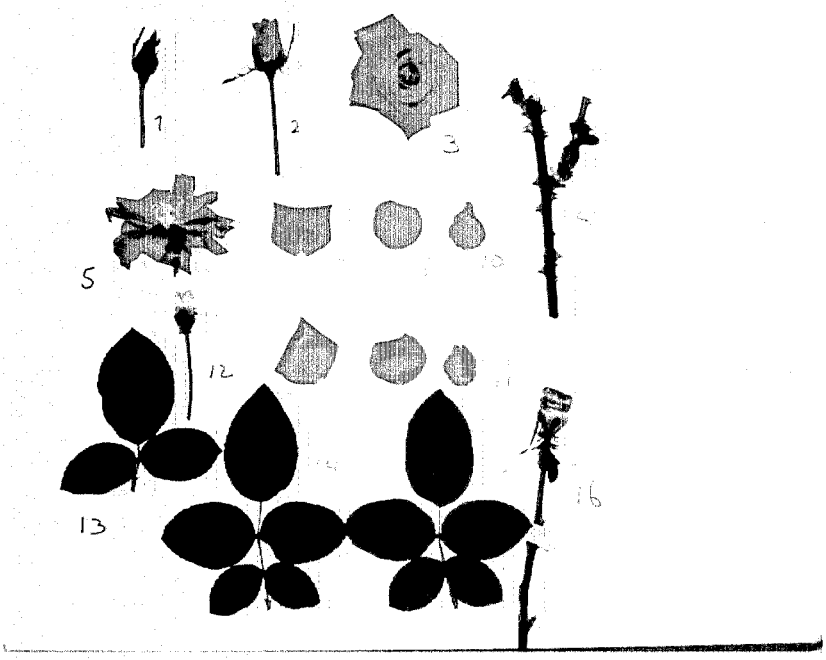
1
2
3
5
12
13
16
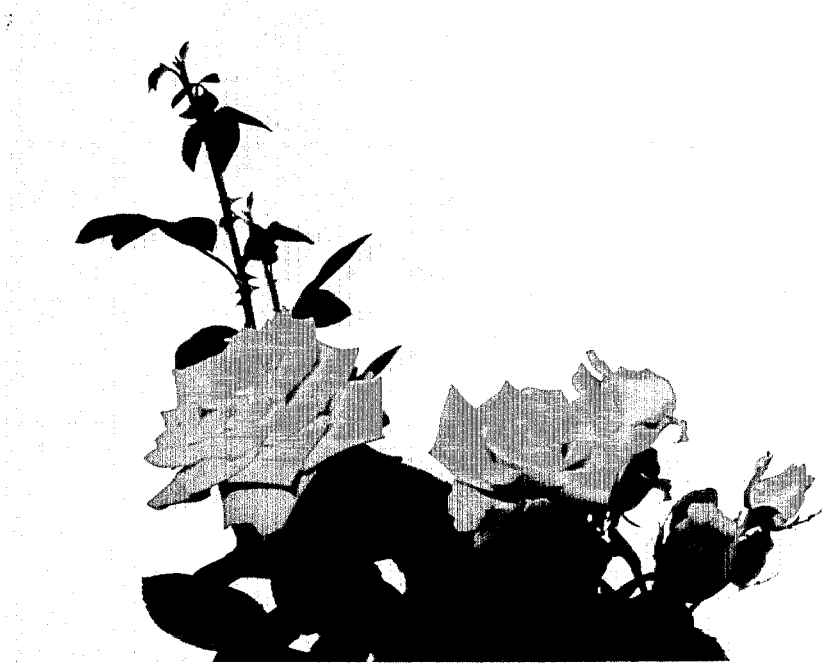

* * * * *